United States Patent [19]
Eaves, III et al.

[11] Patent Number: 6,080,161
[45] Date of Patent: Jun. 27, 2000

[54] FASTENER AND METHOD FOR BONE FIXATION

[76] Inventors: Felmont F. Eaves, III, 4927 Morrowick Rd., Charlotte, N.C. 28226; Peter J. Capizzi, 5924 Marsailles Ct., Charlotte, N.C. 28277

[21] Appl. No.: 09/272,427

[22] Filed: Mar. 19, 1999

[51] Int. Cl.⁷ .................................................. A61B 17/56
[52] U.S. Cl. ............................... 606/76; 606/70; 606/72; 606/77
[58] Field of Search .................................. 606/76, 77, 70, 606/72, 28; 411/501; 623/16

[56] References Cited

U.S. PATENT DOCUMENTS

| | | |
|---|---|---|
| 1,665,216 | 4/1928 | Morton et al. . |
| 3,918,442 | 11/1975 | Nikolaev et al. . |
| 3,981,307 | 9/1976 | Borysko . |
| 4,550,449 | 11/1985 | Tunc . |
| 5,084,050 | 1/1992 | Draenert . |
| 5,120,175 | 6/1992 | Arbegast et al. . |
| 5,163,960 | 11/1992 | Bonutti ..................................... 623/16 |
| 5,290,281 | 3/1994 | Tschakaloff ............................... 606/28 |
| 5,380,221 | 1/1995 | Grabbe . |
| 5,569,250 | 10/1996 | Sarver et al. . |
| 5,578,034 | 11/1996 | Estes . |
| 5,941,901 | 8/1999 | Egan ........................................ 606/72 |

FOREIGN PATENT DOCUMENTS 9201974 1/1994 Netherlands .

Primary Examiner—Michael Buiz
Assistant Examiner—Julian W. Woo
Attorney, Agent, or Firm—Alston & Bird LLP

[57] ABSTRACT

A fastener for securing an osteosynthesis plate to a plurality of bone segments is provided. The fastener in the form of a fastener blank includes an elongated shank adapted for insertion through an opening in the plate and into a hole formed in the bone. The upper end of the shank forms a head that serves to secure the plate to the bone. The elongated shank is constructed of a material which when heated will deform to form a tight fit within the hole drilled in the bone. The fastener is preferably made of a resorbable material. The invention also provides a method for securing a plate to a bone using the fasteners of the invention. A fastener blank is positioned into the hole so that a portion of the blank extends into the hole provided in the bone and another portion overlies the plate. The blank is heated to raise the temperature of the blank above the transition temperature of the material from which it is made and deform the blank into a tight fit within the hole.

11 Claims, 2 Drawing Sheets

FASTENER AND METHOD FOR BONE FIXATION

FIELD OF THE INVENTION

The present invention relates generally to the field of bone fixation. More particularly, the present invention relates to fasteners and methods of using fasteners for securing a fixation plate to bone.

BACKGROUND OF THE INVENTION

The healing of broken bones, especially for cranofacial fractures, requires realignment of the separated or dislocated bone fragments or segments and subsequent fixation for promoting proper healing of the bones. The presence of relative motion of the bone fragments or segments at a fracture or osteotomy site may result in nonunion between the bone fragments and an extension of the time of fracture healing. It is therefore desirable to accomplish as completely as possible an immobilization of the fracture or osteotomy site. This involves the fixation of affected bone segments.

Much progress has been made in recent years regarding the materials for use in fixation plates, the means for fastening the plates to a patient, and methods and systems for attaching plates to a patient. One common type of device and method of fixing resorbable plates to bone involves insertion of screws through the plate into a hole that must be drilled and tapped in the bone itself. Bone screws typically have a headed portion and an elongated threaded shaft to secure the plate to a bone. One of the problems associated with screws is that they tend to shear and are not self-tapping. Bone fixation plates and screws are typically made of metal or resorbable material.

One example of a metal screw is shown in U.S. Pat. No. 5,578,034 to Estes that describes a method of bone fixation. The method of fixation described in Estes uses a metal screw affixed to the bone through the bore of a fixation plate. The system includes a collar recessed into the underside of the fixation plate which prevents the fixation screw from backing out of the bone once it has been affixed.

Another example of a metal fastener is shown in the Arbegast et al patent, U.S. Pat. No. 5,120,175, which provides a fastener made of a shape memory alloy that will self-deploy when heated above a critical martensitic-austenitic phase transformation point. The shape memory alloys include Raychem K-alloy (Ti-Ni-Cu) and nitinol (Ni-Ti). This fastener, however, is not capable of being used for bone fixation due to the necessity to heat the fastener in the manner described.

Fixation of facial fractures and other reconstructive surgery is desirably accomplished using resorbable material. Resorbable plates can be heated, shaped by cutting, and then contoured to fit over the bone being repaired. A surgeon then drills through an opening in the contoured plate to form a hole in the underlying bone. After tapping threads into the hole drilled in the bone, a resorbable screw is used to secure the resorbable plate to a bone. When the screw is completely seated, if it has a hex-head, the head is shorn off leaving the screw head attached to hold the plate against the bone.

An example of a resorbable screw is shown in U.S. Pat. No. 5,569,250 to Sarver et al. This patent describes a system for securing together adjacent bone fragments. Sarver et al. also describe various designs for resorbable bone fixation plates and screws for use in affixing the plates to bone. The resorbable osteosynthesis plates described in the sarver et al. patent may be used with the fasteners of the present invention. Another example of bone fixation devices which are used to secure a fracture in proximity so that it may be healed using resorbable material is disclosed in U.S. Pat. No. 4,550,449 to Tunc, which describes the use of very high molecular weight polymers of L(-) lactide.

There are several problems with the fixation devices described above. First, these devices and the methods used to affix the plates require a surgeon to both drill and tap threads into the bone. Second, these methods require precision between the depth of the tapped hole and the length of the screw, be it metallic or resorbable. If the tapped hole is shorter than the screw, the screw will not seat completely and thus the plate will not be securely held against the bone being repaired. In this event, the screw must be removed and the drilling/tapping process repeated or the screw may break and need redrilling at a different site. In addition, such breakage may require the plate to be repositioned entirely. Third, the process of screwing, especially a resorbable screw, into a threaded bone opening can result in cross threading and/or breaking of the screw during insertion. Another major problem with metal bone fixation devices is the desirability of removing the devices after the bone has completely healed. The surgical procedure necessary for the removal of metal fasteners results in additional trauma to the patient as well as increased medical costs. In addition, metal devices can interfere with X-ray examination of the fracture area.

In accordance with the foregoing, it is a general object of the present invention is to provide an easy to use and effective fastener blank for attaching an osteosynthesis plate to bone.

Another object of the present invention is to provide a resorbable or radiolucent fastener that once in place is operable to secure a biocompatable plate to one or more bone fragments without the need for tapping.

A further object of the present invention is to provide a fastener for use in securing a fixation plate to bone that will be absorbed by the body.

A still further object of the present invention is to provide a method for securely attaching a fixation plate to a patient.

Yet another object of the present invention is to provide a fastener blank and a method for heating the fastener blank to transform the blank into a fastener securing in place a bone fixation plate.

SUMMARY OF THE INVENTION

A fastener and method for securing an osteosynthesis plate to a plurality of bone portions are provided. The fastener in the form of a fastener blank includes an elongated shank having an upper end and a lower end adapted for insertion through an opening in an osteosynthesis plate and into an opening drilled into a bone. The upper end of the shank forms a head that serves to secure the plate to the bone.

The elongated shank is constructed of a material which when heated above the transition temperature of the material will deform to form a tight fit within the hole drilled in the bone. The fastener is preferably made of a resorbable material, most preferably a non-reinforced lactide and glycolide copolymer composition that is non-oriented and has a glass transition temperature of between 55° C. and 62° C. The fastener could also be made of non-absorbable material which can be deformed and which may be polypropylene.

The invention also provides a method for securing or anchoring an osteosynthesis plate having a plurality of openings to a plurality of bone portions using the fasteners of the present invention. In a first embodiment a hole is formed in the bone, such as by drilling. The osteosynthesis plate is positioned so that a hole is substantially coaxial with the hole in the bone. A fastener blank made according to the invention is positioned into the substantially coaxial hole so that a portion of the blank extends into the hole provided in the bone and another portion overlies the osteosynthesis plate. The fastener blank is heated to raise the temperature of the blank above the transition temperature of the material from which it is made and deform the blank into a tight fit within the hole.

In a preferred method, the fastener blank has a hole therein adapted to accommodate a heated wire or filament. The wire is inserted through the fastener blank head and into the shank and heated to melt the fastener material and thereby cause the fastener blank to substantially fill the hole so as to secure the plate to the bone. The fastener blank can also be manufactured with the heating element in place which can then be attached to a device for heating.

In another embodiment, the hole drilled into the bone has a lower portion of a first diameter and a neck portion of a second relatively smaller diameter thereby forming a neck opening having an overhanging rim at the entrance of the hole.

BRIEF DESCRIPTION OF THE DRAWINGS

The foregoing and other objects, advantages and features of the invention, and manners in which the same are accomplished, will become apparent from the following detailed description of the invention taken in conjunction with the accompanying drawings which illustrate preferred and exemplary embodiments, wherein.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

The invention comprises a resorbable fastener and method for in situ formation of the resorbable fastener to secure a bioresorbable plate or other fixture to a bone.

Figure 1:
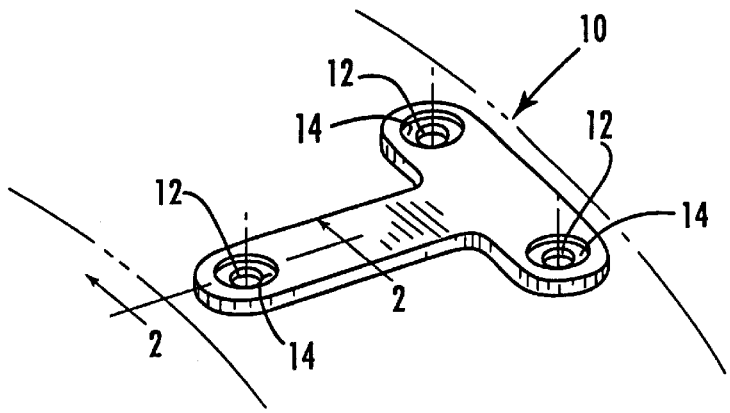
FIG. 1 is a perspective view illustrating an ostosynthesis plate for use with the fasteners of the present invention.
Figure 4:
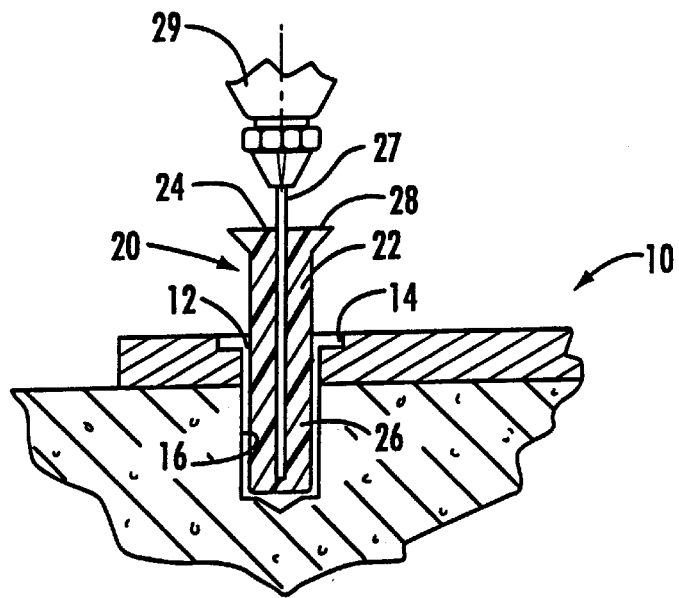
FIG. 4 is a partial side view showing the embodiment of the fastener blank of the present invention having an enlarged head inserted through the plate and into a straight walled hole in the bone.
Figure 5:
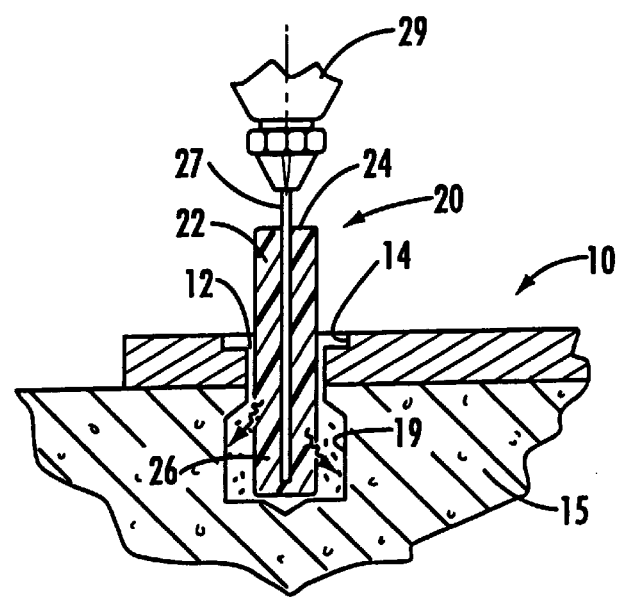
FIG. 5 is a partial side view showing another embodiment of the fastener blank of the present invention inserted through a plate and into a hole having at its lower end a greater diameter than at the neck.

As shown in FIGS. 4 and 5 fastener 20 is provided in the form of a fastener blank being operable to secure an osteosynthesis plate 10, such as the one shown in FIG. 1, having a plurality of openings 12 to a plurality of bone fragments or segments 15. The fastener 20 includes an elongated shank 22 having an upper end 24 and a lower end 26 adapted for insertion into an opening 12 in a bioresorbable plate 10 and then into a hole 16 formed in a portion of bone fragment 15.

The upper end 24 of the elongated shank 22 forms a head which is operable to engage at least a portion of one of said fastener openings formed in the osteosynthesis plate 10. It should be understood that the head 24 may take various shapes and forms. For example the head may be nothing more that the upper end of the shank as shown in FIG. 4. Alternatively, the head 24 may include an extended portion 28 that is larger in diameter than the elongated shank as shown in FIG. 4.

Figure 6:
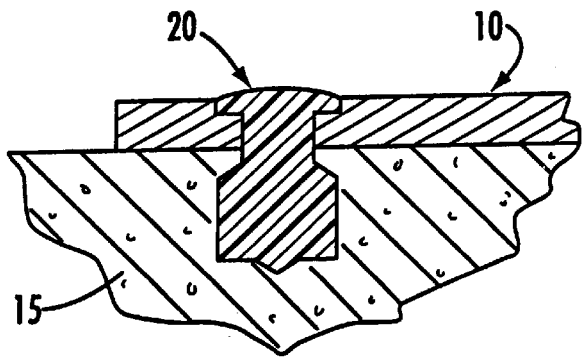
FIG. 6 is a partial side view showing a fastener of the present invention securing a plate to bone in which the fastener blank has been heated to deform the blank to form a tight fit within the hole.

The elongated shank 22 is adapted to accommodate a heat source 28 and constructed of a materials which when the fastener blank is heated above the transition temperature of the material will deform to form a tight fit within the hole formed in the bone as shown in FIG. 6. One feature of the fastener is that the elongated shank 22 may have a hole therein 23 adapted to accommodate a heated wire 27 attached to a heat source 29.

Any material having suitable mechanical and/or bioabsorption properties may be used to accomplish the objects of the present invention. Such materials are resorbed into the body through processes well known to those skilled in the art over a desired period of time. Additional materials, also well known to those skilled in the art which have the appropriate mechanical profile and may or may not be absorbable.

The biocompatible fastener blanks are preferably formed from a non-reinforced lactide and glycolide copolymer composition that is non-oriented and has a glass transition temperature of between 55° C. and 62° C. The copolymer is made from about 70–85% m lactide moieties and from about 15–30% m glycolide moieties having a molecular weight of $M_n$ of generally between 30,000 and 100,000. Such compositions are sold under the name Lactosorb® which may be obtained from Walter Lorenz Surgical, Inc. of Jacksonville, Fla.

According to one aspect of the present invention, a bioresorbable ostosynthesis plate or other material 10, such as the one shown in FIG. 1, is contoured to fit the particular application as is currently done in the art, which may involve heating or other formation means. The plates generally have a plurality of holes or openings 12 to accommodate fasteners. It should be understood that the ostosynthesis plate may take many shapes and sizes. The plates themselves are not part of this invention. The plate 10 is of a preferably thin nature so as to cause a minimum protrusion above the bone surface to which it is affixed. It is preferably made of material that may be resorbed into the body through processes well known to those skilled in the art over a desired period of time. The opening 12 in the ostosynthesis plate 10 may further include a recessed upper face 14. The plate 10 is then operable to accept a plurality of surgical fasteners, such as those described above.

Figure 2:
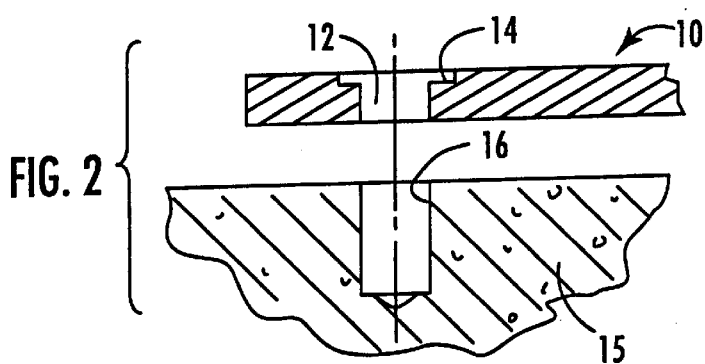
FIG. 2 is a partial side view of the ostosynthesis plate of FIG. 1 taken along line 2—2 thereof and including a portion of a bone having a hole drilled therein according to one method of the present invention.

Another aspect of the present invention is to provide a method for anchoring an osteosynthesis plate having a plurality of openings to a plurality of bone segments. Once the contoured resorbable plate 10 is formed and positioned, the surgeon forms a hole 16 into the bone 15 underlying the plate, such as by drilling, as shown in FIGS. 2 and 4. The surgeon may also form a hole in the resorbable plate itself, or as an alternative, the absorbable plate may include a pre-formed hole. Such drilling is performed through means well known to those skilled in the art. The osteosynthesis plate 10 is positioned so that an opening 12 in the plate is substantially coaxial with the hole 16 in the bone.

The fastener blank 20 is inserted into the substantially coaxial hole so that a portion of the blank extends into the bone and another portion overlies the absorbable structure. The fastener blank 20 is heated to a temperature sufficient to deform the fastener blank and thereby cause the blank to substantially fill the hole so as to secure the plate to the bone.

Figure 3:
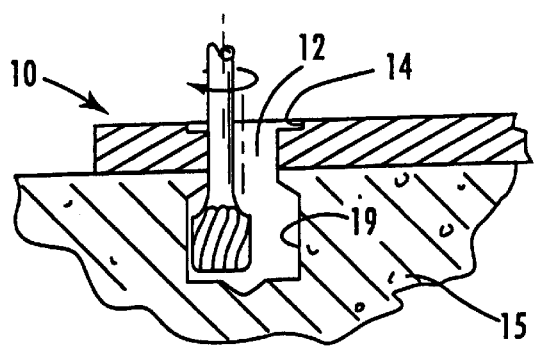
FIG. 3 is a partial side view of an embodiment of the present invention illustrating another drilling method providing an overhanging rim at the entrance of the hole.

A second aspect of the method is shown in FIGS. 3 and 5. After the hole 16 has been formed in the bone a burr or other suitable instrument is used to shape the hole to form a neck opening, such that the lower portion 19 of the hole 16 has a first diameter and the neck portion has a second diameter of a second relatively smaller diameter. The neck opening forms an overhanging rim that may be engaged by the fastener to retain the resorbable plate against the bone segment. After the drilling and burring steps are completed, the resorbable plate 10 is positioned over the hole 16, and the resorbable fastener blank 20 is inserted through the opening 12 so that it extends into the hole 16 in the bone.

A heat source 29 is provided for engaging and melting the fastener blank 20 by suitable means such as electrical resistance via a conducting filament 27, which may be either contained in the fastener blank or integral to the melting apparatus. The melted fastener blank flows so as to conform to the confines of the hole 16 formed in the bone, as shown in FIG. 6. A portion of the blank flows over the outer surface of the resorbable plate 10 and may be contained by the recessed upper face 14 of the plate adjacent hole. This process causes the fastener blank 20 to deform into a rivet-like structure having a shaft portion with a diameter approximately equal to that of the hole 12 and the neck opening of the hole 16 in the bone 15, and two portions having relatively enlarged diameters. One portion conforms to the diameter of the hole in the bone, and the second overlies the resorbable plate in the recessed portion in the plate. When sufficient excess material has formed a head on the outer surface of the resorbable plate, the surgeon may withdraw the melting apparatus and the heating filament. The fastener material then cools so as to harden to form a secure attachment between the plate and the bone.

The heat source 29 may be configured to assist in compression and/or conformation of the fastener. For example, the shaft of the melting filament 27 may consist of an insulated upper portion and a non-insulated lower portion/ forming cup. Electrical power may be supplied to the probe so that it heats the lower shaft and the lower surface of the forming cup. The lower shaft is withdrawn into the probe body leaving the molten fastener material to fill the resulting cavity. The heating device may also have a overlying cap to heat and deform the external end of the fastener, forming it to the plate or fusing it to the plate. If necessary, the heating filament could be designed to withdraw into the heating device to assist in compression and fixation.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A fastener in the form of a fastener blank being operable to secure a material having an opening therethrough to a hole formed in a bone, said blank comprising:

an elongated shank having an upper end and a lower end;

said lower end being adapted for insertion into said opening and a head at said upper end of said elongated shank being operable to engage at least a portion of said fastener opening formed in said material to secure said material to said bone; and said elongated shank being adapted to accommodate a heat source and constructed of a material which when the blank is heated above the transition temperature of the material will deform to form a tight fit within said hole.

2. The fastener according to claim 1 wherein said fastener is made of a resorbable material.

3. The fastener according to claim 1 wherein said fastener is made of a non-reinforced lactide and glycolide copolymer composition which is non-oriented and has a glass transition temperature of between 55° C. and 62° C.

4. The fastener according to claim 1 wherein said head includes an extended portion that is larger in diameter than said elongated shank.

5. A method for anchoring an osteosynthesis plate having a plurality of openings to a plurality of bone portions, comprising:

forming a hole in a bone;

positioning said osteosynthesis plate so that an opening in said plate is substantially coaxial with the hole in said bone portion;

inserting a fastener blank made of resorbable material into the substantially coaxial hole so that a portion of the blank extends into the bone and another portion overlies said osteosynthesis plate; and heating the fastener blank to a temperature sufficient to melt the fastener blank and thereby cause the blank to substantially fill the hole so as to secure the plate to the bone.

6. The method according to claims 5 wherein said blank is heated by a filament inserted into a hole in said fastener blank.

7. The method according to claim 5 wherein said hole formed in said bone has a lower portion of a first diameter and a neck portion of a second relatively smaller diameter.

8. A fastener in the form of a fastener blank being operable to secure a material having an opening therethrough to a hole formed in a bone, said blank comprising:

an elongated shank having an upper end and a lower end;

said lower end of said elongated shank adapted for insertion into said opening, and a head at said upper end of said elongated shank being operable to engage at least a portion of said fastener opening formed in said material to secure said material to said bone; and said elongated shank having a hole therein to accommodate a heated wire and constructed of a material which, when the blank is heated above the transition temperature of the material, will deform to form a tight fit within said hole.

9. The fastener according to claim 8 wherein said fastener is made of a resorbable material.

10. The fastener according to claim 8 wherein said fastener is made of a non-reinforced lactide and glycolide copolymer composition which is non-oriented and has a glass transition temperature of between 55° C. and 62° C.

11. The fastener according to claim 8 wherein said head includes an extended portion that is larger in diameter than said elongated shank.

* * * * *

UNITED STATES PATENT AND TRADEMARK OFFICE
CERTIFICATE OF CORRECTION

PATENT NO. : 6,080,161

DATED : June 27, 2000

INVENTOR(S) : Eaves, III et al.

It is certified that error appears in the above-identified patent and that said Letters Patent is hereby corrected as shown below:

Column 6, line 14, after "material" insert--, said upper end and said lower end--.

Signed and Sealed this

Seventeenth Day of April, 2001

*Attest:*

NICHOLAS P. GODICI

*Attesting Officer*     *Acting Director of the United States Patent and Trademark Office*